United States Patent
Wijnbelt et al.

(10) Patent No.: US 8,088,963 B2
(45) Date of Patent: Jan. 3, 2012

(54) DEHYDRATION OF 1-PHENYL ETHANOL

(75) Inventors: Erik C. Wijnbelt, Barendrecht (NL); Eric H. Hekelaar, Spijkenisse (NL)

(73) Assignee: Lyondell Chemical Technology, L.P., Houston, TX (US)

( * ) Notice: Subject to any disclaimer, the term of this patent is extended or adjusted under 35 U.S.C. 154(b) by 456 days.

(21) Appl. No.: 12/383,347

(22) Filed: Mar. 23, 2009

(65) Prior Publication Data

US 2010/0240939 A1    Sep. 23, 2010

(51) Int. Cl.
*C07C 1/24* (2006.01)

(52) U.S. Cl. .................................... 585/437; 585/436

(58) Field of Classification Search .................. 585/436, 585/437

See application file for complete search history.

(56) References Cited

U.S. PATENT DOCUMENTS

| | | | |
|---|---|---|---|
| 3,351,635 A | 11/1967 | Kollar | |
| 3,442,963 A | 5/1969 | Korchak | |
| 3,526,674 A | 9/1970 | Becker et al. | |
| 3,658,928 A | 4/1972 | Skinner et al. | |
| 5,639,928 A | 6/1997 | Dubner et al. | |

*Primary Examiner* — Thuan Dinh Dang

(57) ABSTRACT

A process for the production of styrene is described. The process comprises dehydrating 1-phenyl ethanol in the liquid phase in the presence of a para- and ortho-toluenesulfonic acid mixture. The ratio of para-toluenesulfonic acid to ortho-toluenesulfonic acid is from 1:9 to 20:1. The process results in reduced heavies production, improved 1-phenyl ethanol conversion and selectivity, less reactor tube fouling, and lower corrosion rates.

6 Claims, No Drawings

DEHYDRATION OF 1-PHENYL ETHANOL

FIELD OF THE INVENTION

This invention relates to a process for producing styrene by the dehydration of 1-phenyl ethanol.

BACKGROUND OF THE INVENTION

Styrene is commercially produced by two main processes: (1) the dehydrogenation of ethyl benzene; and (2) the dehydration of 1-phenyl ethanol. The most commercially successful process to produce styrene utilizing the dehydration of 1-phenyl ethanol has been the process for the co-production of propylene oxide and styrene monomer (the "POSM process"). The POSM process involves the oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to produce styrene monomer. A patent describing this process is U.S. Pat. No. 3,351,635.

The dehydration of 1-phenyl ethanol is a well known reaction. The dehydration process can be performed in the vapor phase and the liquid phase. For example, the vapor phase dehydration of 1-phenyl ethanol is described in U.S. Pat. Nos. 3,442,963 and 3,658,928, and the liquid phase dehydration is described, for example, in U.S. Pat. No. 3,526,674.

Vapor phase dehydration processes typically employ solid catalysts such as titania or alumina. However, these solid catalysts often require frequent regenerations to maintain acceptable conversion and selectivity at high levels. From the standpoint of economics and efficiencies of operation, it is often advantageous to conduct the 1-phenyl ethanol dehydration in the liquid phase in the presence of appropriate catalysts. Although solid catalysts are also useful in the liquid phase dehydration processes, it is preferred to use homogeneous acids such as sulfuric acid, phosphoric acid, and p-toluenesulfonic acid (see, e.g., U.S. Pat. No. 3,526,674). A disadvantage of such technologies is that a certain percentage of the feed material is converted to undesirable by-products such as heavy condensation products, thus lowering the efficiency of the dehydration reaction.

U.S. Pat. No. 5,639,928 describes an improved liquid phase dehydration of 1-phenyl ethanol to styrene monomer. The improvement comprises the use of a residue formation inhibiting agent (nitro substituted phenol or nitro substituted sulfonic acid) during the liquid phase dehydration.

In sum, new and improved processes for the dehydration of 1-phenyl ethanol are needed.

SUMMARY OF THE INVENTION

The invention is a process for producing styrene by the dehydration of 1-phenyl ethanol in the liquid phase in the presence of a para- and ortho-toluenesulfonic acid mixture. The ratio of para-toluenesulfonic acid to ortho-toluenesulfonic acid is from 1:9 to 20:1. The process is effective for reducing the formation of undesirable heavy residue by-products which are normally produced during the dehydration reaction.

DETAILED DESCRIPTION OF THE INVENTION

The process of the invention comprises dehydrating 1-phenyl ethanol to produce styrene. The dehydration of 1-phenyl ethanol is conducted in the liquid phase. The dehydration is preferably performed at temperatures ranging from 180° C. to 300° C., more preferably from 190° C. to 250° C., and most preferably from 200° C. to 230° C. Preferably, the reaction temperature should not be above the decomposition temperature of the liquid phase reaction medium.

The pressure at which the dehydration reaction occurs is not particularly critical, although it is preferred to operate at pressures sufficient to maintain the liquid phase while permitting removal of product water and styrene as vapor. Although atmospheric, super-atmospheric or sub-atmospheric pressures can be used in the process of this invention, it is normally desired to employ pressures which are sub-atmospheric to slightly above atmospheric. Pressures ranging from 100 to 600 millibar (mbar) (10 to 60 kPa), absolute pressure, are more preferred, with pressures ranging from 200 to 300 mbar (20 to 30 kPa) absolute most preferred.

The 1-phenyl ethanol feedstock used in the process of the invention may contain impurities that do not affect the dehydration reaction. For example, the 1-phenyl ethanol stream produced in the POSM process typically contains oxygenated impurities such as acetophenone, 2-phenyl ethanol, and benzyl alcohol. These oxygenated impurities may be present in the 1-phenyl ethanol feed to the dehydration reaction in amounts up to about 15 percent by weight.

During the course of the reaction, 1-phenyl ethanol reacts to form water and the styrene product. At the reaction conditions employed, the water and styrene are preferably volatilized substantially as rapidly as they are formed and are therefore readily removed from the reaction vessel. If 1-phenyl ethanol is also volatilized as the reaction proceeds, it is preferably condensed and returned to the reaction vessel.

The catalyst used in the dehydration reaction is a mixture of para-toluenesulfonic acid and ortho-toluenesulfonic acid. The ratio of para-toluenesulfonic acid to ortho-toluenesulfonic acid is from 1:9 to 20:1, preferably from 1:1 to 8:1, and more preferably from 2:1 to 5:1. The use of a mixture of para- and ortho-toluenesulfonic acid leads to improved yield and corrosion resistance compared to standard para-toluenesulfonic acid catalyst. In addition, the para- and ortho-toluenesulfonic acid mixture decreases the formation of undesirable, heavy residue by-products during the dehydration reaction.

The amount of acid mixture necessary for the process of this invention is not especially critical. Preferably, the para- and ortho-toluenesulfonic acid mixture is used in an amount of at least 10 ppm by weight, more preferably at least 20 ppm by weight, based on the feed to the dehydration, with a preferable maximum of about 150 ppm by weight. Most preferably, the acid mixture is used in an amount ranging from 30 to 100 ppm.

This liquid phase reaction medium can be just the 1-phenyl ethanol feed, but may also include an additional solvent. If used, the solvent preferably has a boiling point that is greater than the boiling point of 1-phenyl ethanol, more preferably at least 10° C. higher and most preferably at least 30° C. higher than that of 1-phenyl ethanol. The solvent can be polar or non-polar, but is preferably non-polar. Suitable non-polar solvents include high boiling hydrocarbons such as triphenylmethane, anthracene, phenanthrene, high-boiling hydrocarbon petroleum distillates such as white oils, mineral oils and other suitable petroleum distillate cuts. Suitable polar solvents include the cresols, pyrocatechol, resorcinol, pyrogallol, 1,2,4-benzenetriol, and phloroglucinol, and their alkyl substituted derivatives. Triphenylmethane is especially preferred.

The process of the invention can be carried out in either batch or continuous manner and is especially suited for continuous operation. In continuous operation, 1-phenyl ethanol space velocities (defined as volumes of 1-phenyl ethanol feed per hour per volume of liquid phase reaction medium) between about 0.1 and about 3 are preferably used to effect substantially complete conversions, i.e., to obtain 1-phenyl ethanol conversions as high as 85% or more. It is more preferred to employ space velocities, based on 1-phenyl ethanol, between about 0.2 and about 2 and it is most preferred to employ such space velocities between about 0.3 and about 1.5.

Since the dehydration reaction is endothermic, control of reaction temperature requires heat input to the reaction. Such can readily be provided by known techniques, for example by inclusion of heating coils within the dehydration reactor.

The dehydration process of the invention produces styrene in high selectivity, with a small quantity of byproducts. The byproducts include ethyl benzene and a heavy residue. The heavy residue is preferentially removed from the liquid phase reaction medium, either periodically or continuously, to prevent the residue from accumulating to an undesirable amount.

The process of the invention preferably results in a reaction selectivity to styrene of at least 92%, as measured by the number of moles styrene formed per mole of 1-phenyl ethanol converted, and an activity of at least 90%, as measured by the number of moles of 1-phenyl ethanol converted relative to the total number of moles of 1-phenyl ethanol in the feed. An activity of at least 92% and selectivity of at least 94% are especially preferred.

The following examples merely illustrate the invention. Those skilled in the art will recognize many variations that are within the spirit of the invention and scope of the claims.

EXAMPLE 1

Dehydration of 1-Phenyl Ethanol

Comparison Example 1A

The dehydration of 1-phenyl ethanol to styrene is conducted in an Alloy 20 reactor (4.3 m I.D.×13 m) and is catalyzed by addition of para-toluene sulphonic acid (pTSA). The reactor is operated at 260 mbara (26 kPa), 204° C., and is heated by 51 bara (5100 kPa) steam via internal exchangers. 1-Phenyl ethanol is fed to the reactor at a rate of 54 ton/hr and pTSA (130 ppm, by weight of the 1-phenyl ethanol feed) is injected via spargers located at the bottom of the reactor. The conversion of 1-phenyl ethanol is controlled at 94% by the addition of pTSA. The vapors are treated in a scrubber to avoid pTSA carry-over and a pTSA containing water stream is returned to the reactor. The catalyst is purged from the bottom of the reactor together with some of the undesired heavy residue.

Example 1B

Comparison Example 1A is repeated with the exception that 45 ppm of a mixture of para-toluenesulfonic acid and ortho-toluene sulphonic acid (oTSA) is used. The ratio of pTSA:oTSA is 80:20.

The results show that the use of the pTSA-oTSA mixture reduces unwanted heavy residue make from 22 kg heavies per ton 1-phenyl ethanol to 16 kg heavies (approximately 25% reduction), corresponding to a 0.7% selectivity improvement. The results also show that less catalyst is required when the pTSA-oTSA mixture is used (45 ppm compared to 130 ppm), showing improved conversion for the pTSA-oTSA mixture. The change to a pTSA-oTSA mixture also reduced the fouling, and therefore lowered the reactor tube skin temperatures at the dehydration reactor heaters significantly (from 260 to 230° C.), thus corresponding to improved corrosion performance. The reduced tube skin temperature correlates to a decrease in corrosion rate of from approximately 10 mils to 2 mils per year and therefore a major increase in reactor life cycle.

The results indicate that the use of a pTSA-oTSA mixture results in reduced production of undesired heavies, improved 1-phenyl ethanol conversion and selectivity, and lower corrosion rates compared to runs using just pTSA.

We claim:

1. A process to produce styrene, which comprises dehydrating 1-phenyl ethanol in the liquid phase in the presence of a para- and ortho-toluenesulfonic acid mixture, having a para-toluenesulfonic acid:ortho-toluenesulfonic acid ratio in the range of from 1:9 to 20:1 to produce a product comprising styrene.

2. The process of claim 1 wherein the ratio of para-toluenesulfonic acid to ortho-toluenesulfonic acid is from 1:1 to 8:1.

3. The process of claim 1 wherein the ratio of para-toluenesulfonic acid to ortho-toluenesulfonic acid is from 2:1 to 5:1.

4. The process of claim 1 wherein the dehydration is performed at a temperature within the range of 180° C. to 300° C. and a pressure within the range of 100 to 600 mbar.

5. The process of claim 1 wherein the para- and ortho-toluenesulfonic acid mixture is used in an amount of at least 20 ppm by weight, based on the total amount of feed to the dehydration.

6. The process of claim 1 wherein the dehydration is performed in the presence of triphenylmethane.

* * * * *